(12) United States Patent
Ingenhoven et al.

(10) Patent No.: US 7,077,940 B2
(45) Date of Patent: Jul. 18, 2006

(54) STRIP HOLDER, CHAMBER, CASSETTE, AND 2-D GEL ELECTROPHORESIS METHOD AND SYSTEM FOR PERFORMING THIS METHOD FOR SEPARATING MOLECULES

(75) Inventors: Nikolaus Ingenhoven, Männedorf (CH); Remo Hoechli, Dürnten (CH); Marcel Rutishauser, Wolfhausen (CH); Anton Posch, Grafing (DE)

(73) Assignee: Tecan Trading AG, Mannedorf (CH)

( * ) Notice: Subject to any disclaimer, the term of this patent is extended or adjusted under 35 U.S.C. 154(b) by 489 days.

(21) Appl. No.: 10/405,688

(22) Filed: Apr. 2, 2003

(65) Prior Publication Data

US 2003/0221962 A1 Dec. 4, 2003

Related U.S. Application Data

(60) Provisional application No. 60/377,318, filed on May 2, 2002.

(30) Foreign Application Priority Data

Apr. 12, 2002 (CH) .................................. 0610/02

(51) Int. Cl.
*B01D 57/02* (2006.01)
*G01N 27/26* (2006.01)

(52) U.S. Cl. ...................... 204/466; 204/456; 204/462; 204/610; 204/613; 204/616; 204/623; 422/50

(58) Field of Classification Search ................ 204/456, 204/459, 462, 466, 548, 606, 608, 610, 613, 204/616, 620, 621, 623, 467; 422/50

See application file for complete search history.

(56) References Cited

U.S. PATENT DOCUMENTS

4,999,340 A * 3/1991 Hoffman et al. ............... 514/23

(Continued)

FOREIGN PATENT DOCUMENTS

EP 88401924.1 7/1988

(Continued)

*Primary Examiner*—Nam Nguyen
*Assistant Examiner*—Anthony Fick
(74) *Attorney, Agent, or Firm*—Notaro & Michalos, PC

(57) ABSTRACT

A strip holder (1) is disclosed for accommodating a gel strip (3) for separating molecules using gel electrophoresis. The strip holder (1) disclosed is distinguished by including a baseplate (4), at least one stop (5), which is offset to a lower level in relation to the carrier surface (2), and at least one sealing surface (6), this stop (5) being implemented to be applied to counter surfaces (7) of an electrophoresis chamber, through which offset to a lower level of the stop (5) the installation depth of the strip holder (1) carrying a gel strip (3) into this electrophoresis chamber is determined and the sealing surface (6) ensuring a sealing installation of the strip holder (1) carrying a gel strip (3) into this electrophoresis chamber. Such a chamber (15) for isoelectric focusing of molecules in gel strips (3) is distinguished by including such a strip holder (1), a frame (16), and a cover (20). Another chamber in the form of a cassette (33), for performing an electrophoresis in the second dimension following the isoelectric focusing, includes two plates (34, 35) and at least one seal (36) which separates these plates and is distinguished by including such a strip holder (1), the strip holder being sealingly inserted into a recess (37) in one of these plates (34). The first dimension of a corresponding 2-D gel electrophoresis method is also disclosed.

19 Claims, 3 Drawing Sheets

U.S. PATENT DOCUMENTS

| | | |
|---|---|---|
| 6,113,766 A | 9/2000 | Steiner et al. |
| 6,179,980 B1 * | 1/2001 | Aksberg ..................... 204/616 |
| 2001/0037940 A1 * | 11/2001 | Shih et al. .................. 204/466 |

FOREIGN PATENT DOCUMENTS

| | | |
|---|---|---|
| WO | PCT/US98/07387 | 4/1998 |
| WO | PCT/US01/11599 | 4/2001 |

* cited by examiner

Fig. 3
Fig. 4
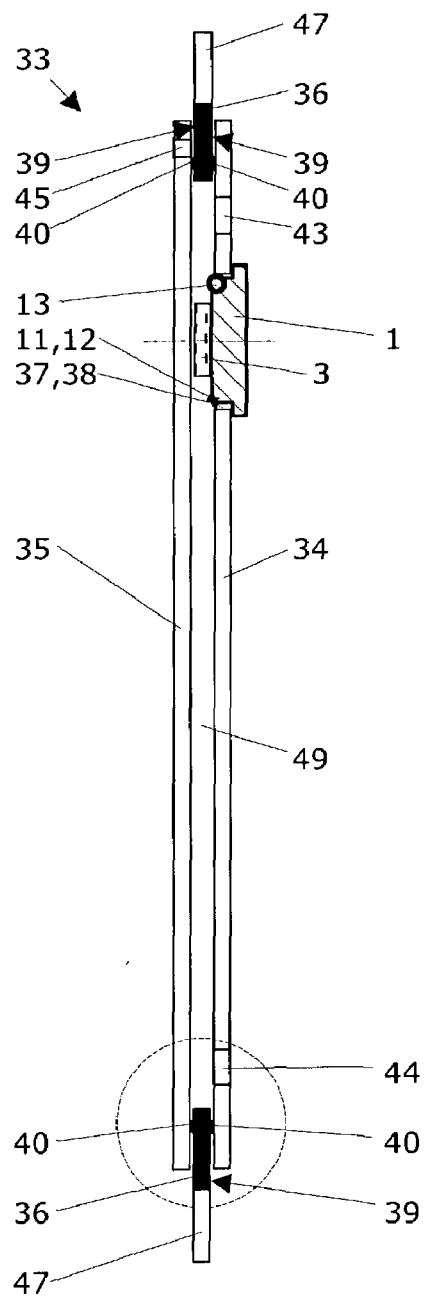
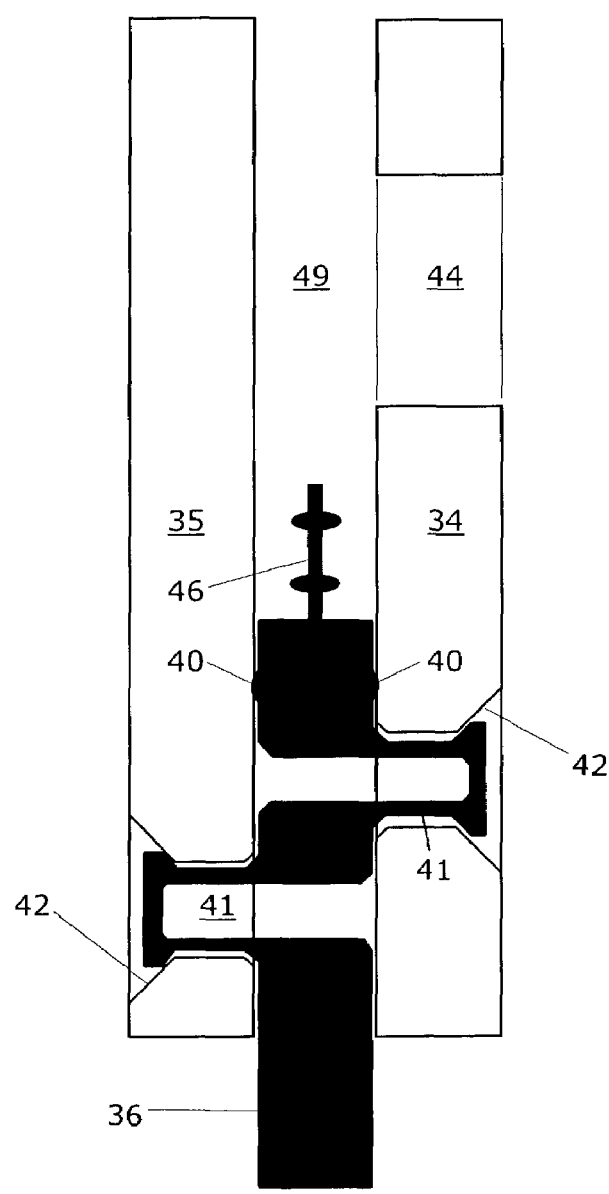

US 7,077,940 B2

STRIP HOLDER, CHAMBER, CASSETTE, AND 2-D GEL ELECTROPHORESIS METHOD AND SYSTEM FOR PERFORMING THIS METHOD FOR SEPARATING MOLECULES

RELATED PATENT APPLICATION DATA

This application claims priority of the Swiss Patent Application No. 0610/02 filed on Apr. 12, 2002 and of the U.S. Provisional Application No. 60/377,318 filed on May 2, 2002.

FIELD OF THE INVENTION

The present invention relates to a strip holder having a baseplate including a carrier surface—for accommodating a gel strip for separating molecules using gel electrophoresis—; as well as a chamber for isoelectric focusing (IEF) of molecules in gel strips; a gel electrophoresis cassette for performing electrophoresis in a second dimension following the IEF, which includes two plates and at least one seal separating these plates; a corresponding 2-D gel electrophoresis method and a system for automatically performing the method.

BACKGROUND OF THE INVENTION

More than 25 years ago, O'Farrell [O'Farrell P H. *J. Biol. Chem.* 1975, 250:4007–4021] published a method for high-resolution separation of proteins of the bacteria *Escherichia coli* using two-dimensional polyacrylamide gel electrophoresis (2-D PAGE). In the meantime, this method has been refined and today it is one of the most applied techniques for the analysis and characterization of complex protein mixtures.

The application of isoelectric focusing (IEF) as the first step of 2-D PAGE allows the separation of the proteins on the basis of their charge, and may be performed in polyacrylamide gels with or without an immobilized pH gradient [cf. Görg A., Postel W., and Günther S. The current state of 2-dimensional electrophoresis with immobilized pH gradients. *Electrophoresis* 1988, 9:531–546]. In the second step, polyacrylamide gels, which contain sodium dodecyl sulfate (SDS) as an anionic detergent and which are particularly suitable for separating proteins on the basis of their molecular weight, are preferably used. Therefore, 2-D PAGE is capable of separating proteins on the basis of two independent parameters, charge and size.

A device for rehydrating a gel strip and performing an IEF as a first step of a 2-D PAGE is known from U.S. Pat. No. 6,113,766. The device includes a chamber which is suitable both for rehydrating a prefabricated and dried gel strip and for performing the IEF. For this purpose, the gel strip is placed in the chamber in such way that—gel side down— each of its end regions comes to rest on one electrode in the chamber floor. The chamber is sealable using a cover, which exercises a specific pressure on the gel strip via pressure parts, so that the gel is pressed onto the electrodes. Following the IEF, i.e., the separation of the proteins in a first dimension, the gel strip is removed from the chamber and laid on an SDS-polyacrylamide gel for performing the separation of the proteins in the second dimension. The gel strip may be damaged as this is done, which may endanger the success of the entire 2-D gel electrophoresis. In addition, achieving a pressure which is sufficiently large to ensure the electrical contact for the IEF, but is small enough that the gel is not damaged is extremely difficult and complicated, because the degree of rehydration of the IEF gel additionally influences its volume.

A solution of the first problem described is known from German Patent 198 31 210, in which a practically simultaneous casting of the gel for the first and second dimension in a joint device is disclosed. The IEF gel is only separated from the SDS-PAGE gel by a narrow element, which may be removed after completion of the IEF and thus leaves a space open which may be filled with a contact gel to bring both gels into contact. The SDS-PAGE may be performed after this. This solution has the advantage that the IEF gel strip does not have to be touched or transported at all between the first and second dimension of a 2-D PAGE. However, it is disadvantageous that both gels must be discarded if the IEF is not successful. In addition, it is known that the reproducibility of IEF results is significantly improved if IEF gels of the same batch are used. This would mean that a large number of gels for the first and second dimension would have to be cast at the same time and under the same conditions, which may become very costly.

Another solution of the first problem described is disclosed in U.S. Pat. No. 5,993,627. In a fully automated system for performing 2-D gel electrophoresis, gels for both the first and the second dimension are cast. The system also includes devices for performing the electrophoresis, the subsequent gel staining, and the analysis. The system is based on the production of IEF gels on a "backing material" made of Gelbond®, from the transfer of this gel into a mold for casting the SDS gel, into which a massive electrode is also cast simultaneously. The system requires multiple robot arms and/or gripping tools for grasping and transporting the gels from one container (IEF chamber) to the other (SDS-PAGE chamber, staining chamber, and scanning bed). The Gelbond® material does improve the stability of the IEF strip, but the method suggested is complicated and costly, and the system is correspondingly expensive.

SUMMARY OF THE INVENTION

The present invention has the object of providing an alternative device which removes or at least minimizes the disadvantages known from the related art.

BRIEF DESCRIPTION OF THE DRAWINGS

The present invention will now be described in more detail with reference to schematic and exemplary drawings, which are not to restrict the extent of the present invention.

FIG. 3 shows a perpendicular cross-section through an SDS-PAGE cassette having an inserted strip holder and IEF gel;

FIG. 4 shows an enlarged detail section (cf. circle in FIG. 3) through the seal of the SDS-PAGE cassette;

DETAILED DESCRIPTION OF THE INVENTION

Figure 1:
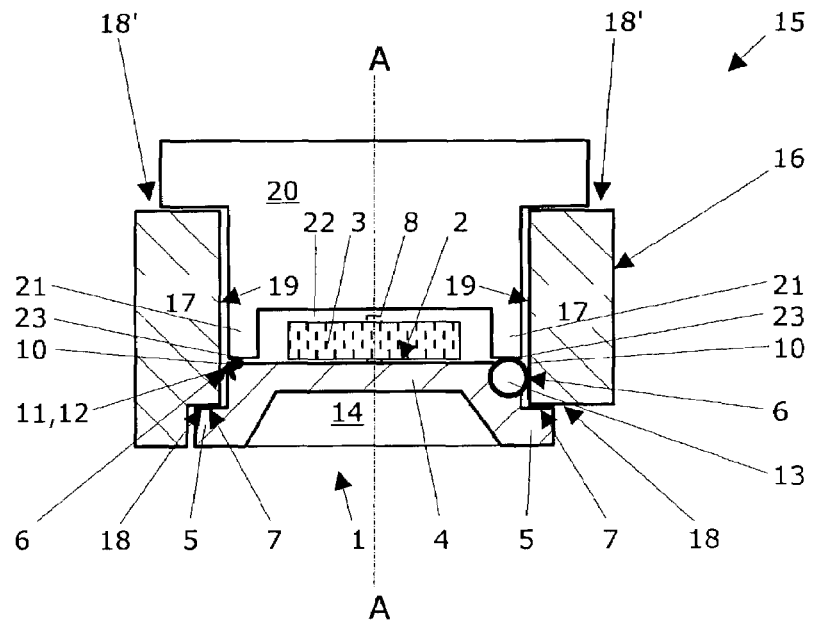
FIG. 1 shows a perpendicular cross-section through a closed IEF chamber having an IEF gel strip inserted.

FIG. 1 shows a strip holder 1 having a baseplate 4 which includes a carrier surface 2 for accommodating a gel strip 3 for separating molecules using gel electrophoresis. Baseplate 4 includes at least one stop 5, which is offset to a lower level in relation to carrier surface 2, and at least one sealing surface 6. This stop is implemented to be applied to counter surfaces 7 of an electrophoresis chamber, through which the installation depth of strip holder 1, which carries a gel strip 3, into this electrophoresis chamber is determined and the sealing surface 6 ensuring a sealed installation of strip holder 1, which carries a gel strip, into this electrophoresis chamber.

Stop 5 is implemented in one piece with baseplate 4 in this case and forms a continuous peripheral stop surface. Alternatively, it may be provided (not shown), that the stop surface is subdivided or replaced by a bow attached to baseplate 4 with the same effect. While baseplate 4 is preferably manufactured from a chemically inert, electrically insulating material having good thermal conduction properties, such bows may be produced from another material (e.g. from metal) and, for example, be cast into or screwed onto the baseplate.

Baseplate 4 preferably has one perpendicular pin 8 in the region of each of the two carrier surface ends, which are implemented for the penetrative positioning of gel strip 3. In addition, the baseplate may have depressions 9 for accommodating buffer solution outside carrier surface 2 for gel strip 3.

Sealing surface 6 may be implemented as a lip seal 11, molded onto outermost, upper edge 10 of the baseplate, having one or two sealing lips 12. This lip seal 11 is preferably produced in one piece with strip holder 1 in a two-component injection molding method, sealing lips 12 preferably being produced from a more elastic plastic than strip holder 1. Alternatively to a lip seal which is sprayed on, an O-ring 13 may also be positioned in place of lip seal 11, in this case—depending on the material of the strip holder— O-ring 13 may be laid in a peripheral groove or sprayed onto the strip holder and/or produced together with the strip holder in a two-component injection molding method. Embodiments which favor cost effective mass production of strip holders conceived as consumables are preferred.

As already noted, baseplate 4 is preferably manufactured from a chemically inert, electrically insulating material (IEF is routinely performed at approximately 15 kV), plastics which are capable of being injection molded being particularly preferred in this case. Baseplate 4 is also to have good thermal conduction properties, so that during the rehydration of the IEF gel and, above all, during the IEF gel electrophoresis, the temperature of the gel may be controlled better. For this purpose, the baseplate preferably has a lower hollow 14 for accommodating a cooling rib (not shown) of a cooling unit. Further preferred features of baseplate 4 include good cold resistance, so that—after electrophoresis has been performed in the first dimension—IEF gels 3 may be frozen together with strip holder 1, stored deep-frozen at approximately −80° C. for almost any desired length of time, and thawed as needed and used for the second dimension of the 2-D electrophoresis. For this purpose, the strip holder is preferably produced from a non-hygroscopically active material, so that the dimensional accuracy of strip holder 1 is not impaired by repeated freezing and thawing.

Furthermore, FIG. 1 shows a chamber 15 for the isoelectric focusing (IEF) of molecules in gel strips 3. This chamber includes a strip holder 1 and a frame 16 having a peripheral wall 17 and an upper and lower counter surface 18, 18'. Strip holder 1 is inserted into frame 16 in such a way that the at least one stop 5 is applied to counter surface 18 and lower sealing lip 12 presses tightly against an inner surface 19 of wall 17. The chamber also includes a cover 20 to be applied to upper counter surface 18' of frame 16.

Cover 20 preferably has a bead in the form of a peripheral rib 21 which projects into chamber 15 and limits inside 22 of the chamber over gel strip 3. At the same time, outermost lower edge 23 of bead 21 is applied to a sealing lip 12 of lip seal 11 to form a seal. Alternatively, lower edge 23 of bead 21 is also applied to an O-ring 13 attached to strip holder 1. The cover is preferably provided with contact pins or other suitable, removable contact means (not shown), so that the circuit, for the safety of the operator, is only closed when chamber 15 is sealed and is automatically interrupted when the chamber is opened.

Figure 2:
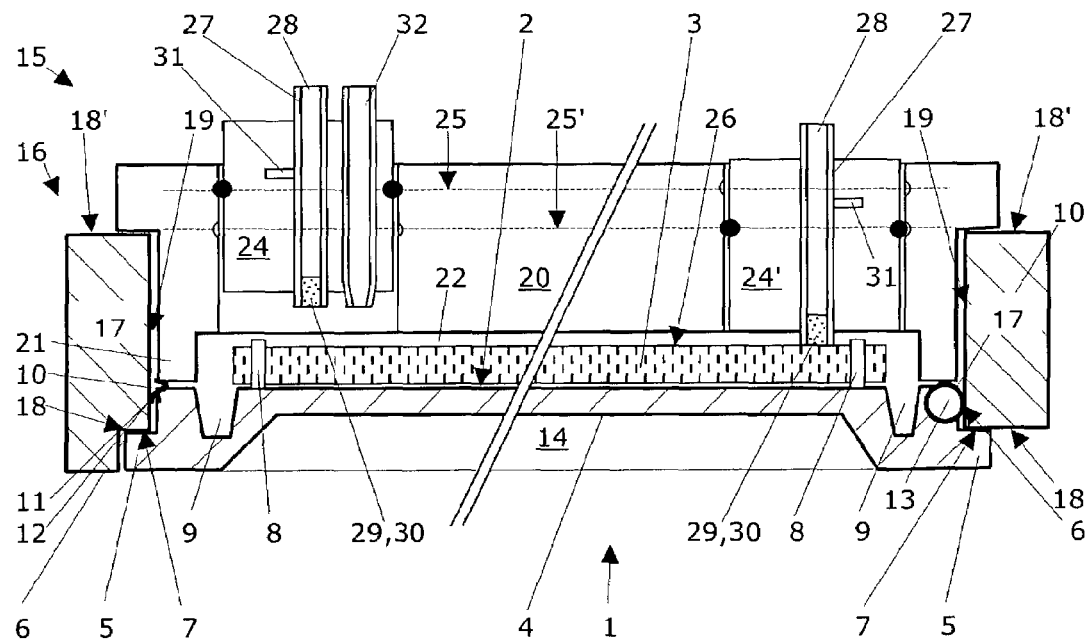
FIG. 2 shows a perpendicular longitudinal section through a closed IEF chamber having a gel strip inserted, along section line A—A in FIG. 1.

FIG. 2 shows a perpendicular longitudinal section through a closed IEF chamber having a gel strip inserted. The section runs along the section line indicated in FIG. 1 with A—A. Two electrode holders 24, 24' may be inserted into cover 20. These electrode holders are preferably implemented so they are insertable into two defined levels 25, 25' and each include an electrode 27, which has limited movability perpendicular to surface 26 of a gel strip 3 lying on carrier surface 2 of strip holder 1. These electrodes 27 are implemented as small tubes made of electrically nonconductive material (e.g. glass, plastic, ceramic) having one open upper opening 28 and have a frit 30 which partially seals lower opening 29. Alternatively, conductive material may also be used for the tubes. Electrodes 27 also have a laterally branching electrical contact 31. The hollow electrodes may be at least partially filled with buffer solution and thus represent an electrically conductive connection between a high voltage control (not shown) and the two poles of a gel strip 3. Frit 30 is a filter, which is permeable to the buffer and to ions or excess proteins migrating to electrodes 27 during the IEF, and which prevents crystallization of these particles on the electrodes due to its permeability.

Especially in devices for automated performance of IEF electrophoresis, a reduced rate of contamination and/or simpler cleaning is appreciated thanks to these electrodes 27. In spite of this permeability, frit 30 represents a flow resistance for the buffer in the tube which is great enough that it may not run out spontaneously due to its hydrostatic pressure.

As an alternative to the open version described, the electrode tubes may be sealed on their upper end except for a supply line (inlet, not shown). An outlet is then positioned in place of laterally branching electrical contact 31. The inlet and outlet are then connected to a circulation system for temperature control and/or filtration of the buffer. The electrical connection to a suitable high voltage control is then also produced via the inlet or outlet.

The first part (first dimension) of a 2-D gel electrophoresis method using strip holder 1 and/or chamber 15 according to the present invention preferably runs as follows:

A dehydrated gel strip 3 is positioned on carrier surface 2 of a strip holder 1.

This strip holder 1 is inserted into a frame 16, having a peripheral wall 17 and an upper and lower counter surface 18, 18', in such a way that the at least one stop 5 is applied to lower counter surface 18 and sealing surface 6 presses tightly against an inner surface 19 of wall 17.

Gel strip 3 inside this chamber 15 is layered with rehydration solution. Alternately, gel strip 3 may be layered with oil before the application of the sample to avoid evaporation losses. In this case, a sample may already be contained in this rehydration solution; if this is not the case, the sample may be applied to the gel strip and/or introduced into the gel strip later (preferably in a strip shape with the chamber open or via a sample tube 32 with the chamber closed and the high voltage switched on; cf. below).

The chamber is closed using a cover 20 to be applied to upper counter surface 18' of frame 16 and two electrode holders 24, 24' insertable in this cover 20. In this case, the electrode holders are inserted into an upper level 25, due to which one electrode 27 at a time, which are each restrictedly movable perpendicular to surface 26 of a gel strip 3 lying on the carrier surface 2 of strip holder 1, is positioned at a distance to this surface 26.

After the sample is diffused into the gel, the electrode holders are lowered to a lower level 25', due to which both electrodes 24, 24' come into contact with this surface 26 of gel strip 3.

Gel strip 3 is subjected to electrical high voltage via electrodes 24, 24' until the isoelectric focusing (IEF) of the molecules in the gel has occurred. In this case, the electrical high voltage is preferably generated using a single channel control device, which regulates the electrical current parameters and in addition stores them so they may be called up and, for example, displayed on a display screen.

The application of the sample onto the gel may—according to a first variant of the method according to the present invention—be performed by applying the sample in a strip shape onto gel 3 when chamber 15 is opened. This is preferably performed using a pipettor, which may reproducibly dispense a specific quantity of sample. Chamber 15 is then closed using a cover 20 to be applied to upper counter surface 18' of frame 16 and two electrode holders 24, 24' which are insertable in this cover 20. In this case, the electrode holders are inserted into an upper level 25, due to which one electrode 27 at a time, which are each restrictedly movable perpendicular to surface 26 of a gel strip 3 lying on the carrier surface 2 of strip holder 1, is positioned at a distance to this surface 26, until the sample has diffused into the gel. The restricted movability of the electrodes in the Z direction described may be produced in various ways. Electrodes 27 may be freely guided in the Z direction (perpendicular to the surface of the IEF gel, which lies essentially horizontally), so that they are applied to the IEF gel with their intrinsic weight (including tube, frit, and buffer filling). Electrodes 27 may adjusted in their Z position using one or more spring elements (not shown) in such a way that they are applied to the IEF gel surface with a defined pressure. The Z movability of the electrodes is therefore restricted on one side by at least one spring element and/or one end stop (both not shown), so that the electrodes may not come into contact with gel surface 26 if electrode holder 24, 24' is inserted in upper level 25. Both variants of the Z movability allow soft but reliable contact with the gel surface, so that the electrical contact for the IEF is ensured without the gel being damaged. Electrode holders 24, 24' are subsequently lowered to a lower level 25', due to which both electrodes 27 come into contact with this surface 26 for performing the IEF.

The application of the sample onto the gel may—according to second variant of the method—be performed by closing chamber 15 using a cover 20 to be applied to upper counter surface 18' of frame 16 and two electrode holders 24, 24' which are insertable in this cover 20, in that the electrode holders are inserted directly into a lower level 25'. In this way, one electrode 27 at a time and at least one sample tube 32, all of which are restrictedly movable perpendicular to surface 26 of a gel strip 3 lying on the carrier surface 2 of strip holder 1 (cf. variant 1), come into contact with this surface 26. Subsequently, the sample is drawn into the gel strips from sample tube 32 while an electrical voltage is applied over the gel.

The performance of this method in an appropriate automatic system (not shown) is especially preferred, in this case, this system may include a working platform for arranging one or more IEF chambers and may be equipped with a cooling device for cooling the IEF chambers. Such a system preferably also includes a robot arm for transferring individual parts of the chamber to and from these IEF chambers and/or SDS-PAGE cassettes, as well as a computer for controlling the robot, a single-channel high voltage control for individual control of the IEF chambers, and a display screen. Using such a system, which preferably also includes a pipettor having multiple channels, the rehydration solution may also be supplied automatically and in a defined quantity, so that no excess rehydration solution must be removed from the chamber. If required, this method can be stopped after having performed the first dimension electrophoresis.

FIG. 3 shows a perpendicular cross-section through an SDS-PAGE cassette 33 for performing electrophoresis in a second dimension, following the isoelectric focusing, having an inserted strip holder 1 and a IEF gel strip 3. This cassette 33 includes two plates 34, 35 and at least one seal 36 separating these plates. A strip holder 1 is inserted into a recess 37 in one of these plates 34 in such a way that the at least one stop 5—preferably set off to a lower level by the dimension of the plate thickness—is applied to the outer surface of plate 34, which acts as a counter surface 7, and sealing surface 6 presses tightly against inner surface 38 of recess 37. In this case, gel strip 3 almost fills up space 49 between plates 34, 35 and carrier surface 2 is essentially flush with the inner surface of front plate 34.

Seal 36 is implemented as an essentially flat, one-piece, annular seal, which is essentially positionable in the region of the outer edge of plates 34, 35, with seal 36 including an annular, peripheral, elastically deformable sealing edge 40 on each of sides 39, which press against the plates. Seal 36 also includes attachment nubs 41, lying in the region outside its sealing edge 40, which are implemented to be snapped into corresponding holes 42 incorporated into both plates 34, 35.

At least one of the plates (in this case front plate 34) includes first openings 43, positioned in the region of the space defined inside sealing edge 40, for introducing a gel, buffer, or stain and/or second openings 44 for ventilation or for introducing a gel, buffer, or stain. Front and back plates 34, 35 also include, positioned inside the region of the space covered by seal 36, third openings 45 for introducing a separating medium.

FIG. 4 shows an enlarged detail section (corresponding to the circle in FIG. 3) through the seal of an SDS-PAGE cassette 33. Essentially flat seal 36 is essentially positioned in the region of the outer edge of plates 34, 35 and has an annular, peripheral, elastically deformable sealing edge 40 on each of sides 39, which press against the plates 34, 35. Attachment nubs 41, which lie in the region outside their sealing edge 40, are positioned alternating, so that the seal may be removed from the mold easily after the manufacturing process for its production (e.g. injection molding). In spite of this, two attachment nubs 41 are always positioned so near one another that they act like a direct connection between plates 34, 35. When cassette 33 is assembled, the snapping of attachment nubs 41 into holes 42 of plates 34, 35 provided for them has the effect that the three main elements are provisionally held together and seal 36 remains correctly positioned during installation of cassette 33 into a holding device (not shown).

Plates 34, 35 are preferably produced from glass. Seal 36 preferably has an elasticity which essentially corresponds to that of an SDS gel, the toughness of the seal, however, being greater than that of the gel. In order that the SDS gel does not have to be grasped and/or in order that the SDS gel may be handled carefully, seal 36 includes clips 46 to be polymerized into such a gel. These clips preferably have a relief pattern (having a network structure, holes, nubs, and the like), which is suitable for producing intimate contact with the SDS gel. A chemical bond is preferably produced between the gel and the clips of the seal.

Figure 5:
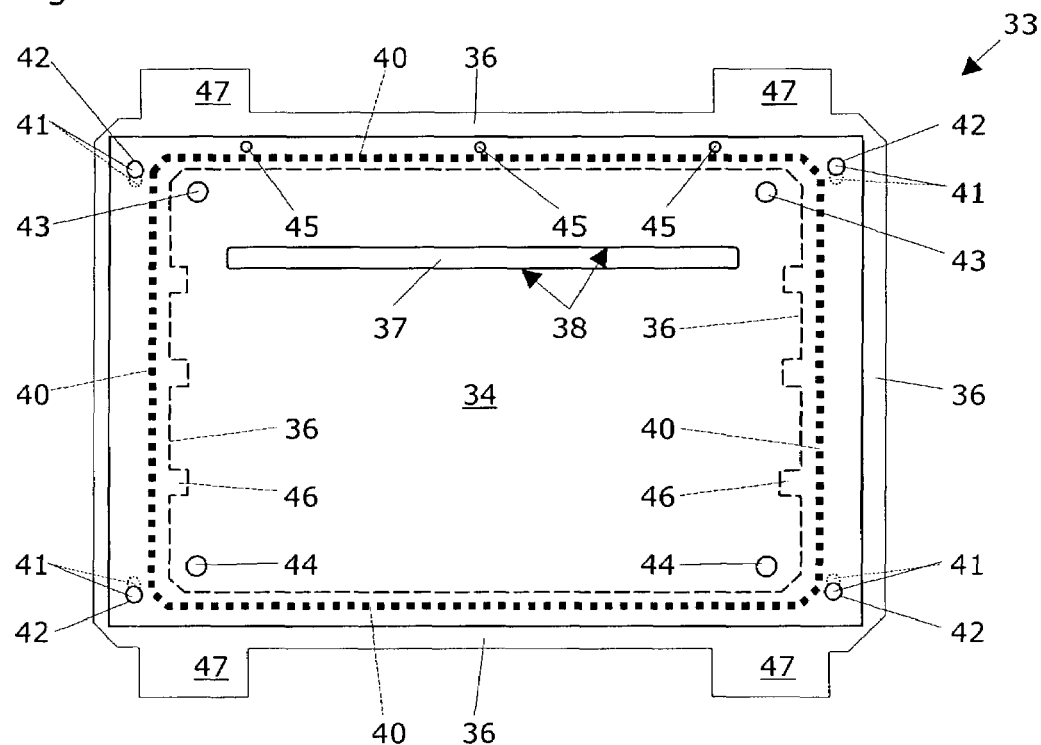
FIG. 5 shows a top view of the front plate of an assembled SDS-PAGE cassette before the insertion of a strip holder.

FIG. 5 shows a top view of front plate 34 of an assembled SDS-PAGE cassette 33 before the insertion of a strip holder 1. Recess 37 for inserting strip holder 1 is in the upper half of cassette 33, which is preferably used in this perpendicular position for the SDS-PAGE. Front plate 34 preferably has first openings 43 and/or second openings 44, positioned in the region of the space defined inside sealing edge 40, for ventilation or for introducing a gel, buffer, or stain. In addition, third openings 45 for introducing a separating medium are preferably positioned in the region of the space covered inside seal 36. This separating medium may be a gas (air, nitrogen, etc.) or a liquid (e.g. buffer) and is used for careful removal of the PAGE gel from plate 34, so that this surface of the PAGE gel may subsequently be subjected to a staining solution.

Seal 36 is essentially positionable in the region of the outer edge of plates 34, 35, includes annular, peripheral, elastically deformable sealing edge 40 described, and preferably projects all around plates 34, 35 over their outermost edge to protect plates 34, 35, which are preferably made of glass. Seal 36 is essentially implemented as flat, one-piece, and annular, it defines the interval between front plate 34 and back plate 35 and preferably has an elasticity which essentially corresponds to that of an SDS gel, the toughness of the seal, however, being greater than that of the gel. For a close connection between seal and SDSPAGE gel, seal 36 has clips 46 to be polymerized into such a gel. The seal is therefore used as a frame for holding the gel, which must never be touched directly. For grasping the seal using a tool and/or a robot, it preferably has holding straps 47 on its outside. In the region outside its sealing edge 40, seal 36 includes attachment nubs 41 which are implemented to be snapped into corresponding holes 42 incorporated into both plates 34, 35.

A cassette 33 provisionally assembled (preferably by hand) includes a front plate 34, a back plate 35, and a seal 36, positioned between them and connecting both plates 34, 35. Such a cassette may also be transported with the aid of a robot, in that the robot grasps the holding straps using suitable means; for this purpose, seal 36 holds both plates 34, 35 together with sufficient security via its nubs 41.

Figure 6:
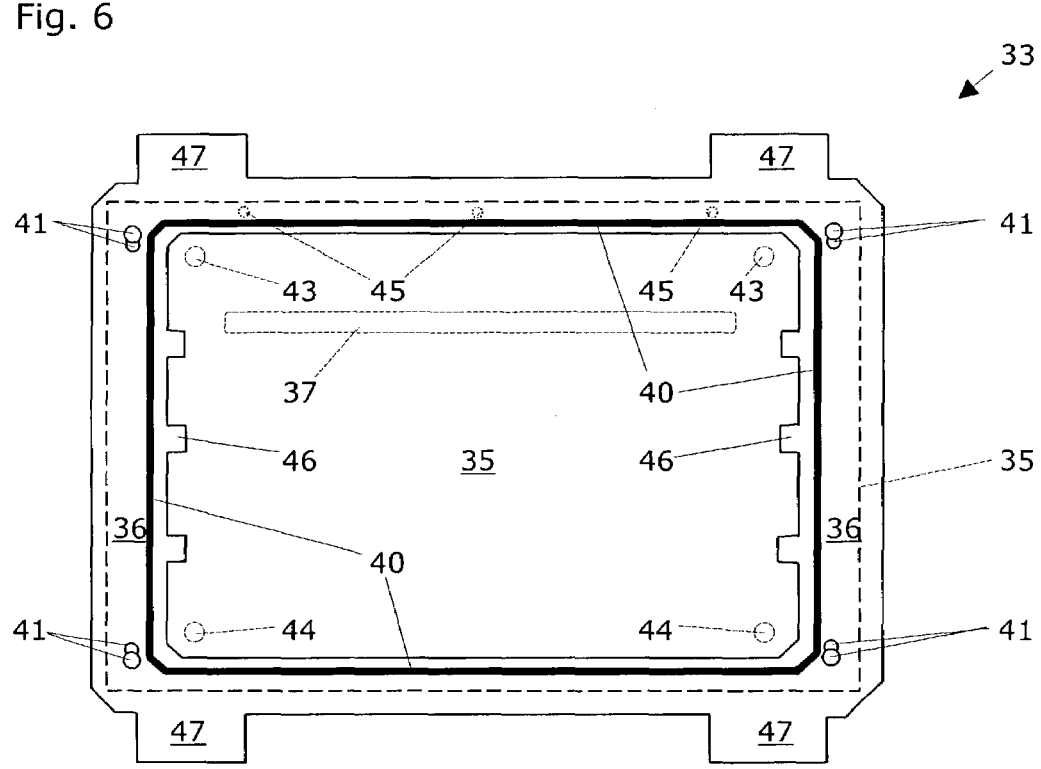
FIG. 6 shows a frontal view of an assembled SDS-PAGE cassette with the front plate removed.

FIG. 6 shows a frontal view of an assembled SDS-PAGE cassette 33 with the front plate removed; recess 37 and first openings 43 and/or second openings 44 of front plate 34 are only indicated with dashes. In addition, third openings 45 for introducing a separating medium are preferably positioned in the region of the space covered inside seal 36. This separating medium may be a gas (air, nitrogen, etc.) or a liquid (e.g. buffer) and is used for careful removal of the PAGE gel from back plate 35, SO that this surface of the PAGE gel may subsequently be subjected to, for example, a staining solution.

The working platform of a system for automatically performing the 2-D gel electrophoresis method preferably includes eight IEF chambers arranged in parallel to one another, so that the cooling unit preferably used for temperature control of the IEF chambers also has eight cooling ribs. The single-channel control device for the high voltage is preferably accordingly laid out for the individual control of eight IEF chambers and, in addition, stores the electrical current parameters of all eight IEF chambers of the automatic system so they may be called up and, for example, displayed on a display screen.

The reference numbers refer to the same features in each case, even if all features are not expressly described for every figure.

What is claimed is:

1. A strip holder having a baseplate, including a carrier surface for accommodating a gel strip for the separation of molecules using gel electrophoresis,
    wherein the baseplate includes at least one stop, which is offset to a lower level in relation to the carrier surface, and at least one sealing surface, this stop being implemented to be applied to counter surfaces of an electrophoresis chamber, through which offset to a lower level of the stop the installation depth of the strip holder carrying a gel strip into this electrophoresis chamber is determined and the sealing surface ensuring a sealing installation of the strip holder carrying this gel strip into this electrophoresis chamber, and wherein the at least one stop is implemented in one piece with the baseplate and forms at least one stop surface.

2. The strip holder according to claim 1,
    wherein the baseplate has a perpendicular pin in the region of each of the two ends of the carrier surface, which is implemented for penetrative positioning of the gel strip, and the baseplate has depressions outside the carrier surface for accommodating buffer solution.

3. The strip holder according to claim 1,
    wherein the sealing surface is implemented as a lip seal, molded onto the outermost upper edge of the baseplate, having one or two sealing lips.

4. The strip holder according to claim 1,
    wherein the baseplate is manufactured from a chemically inert, electrically insulating material having good thermal conduction properties and has a lower hollow for accommodating a cooling rib of a cooling unit.

5. A chamber for the isoelectric focusing of molecules in gel strips,
    wherein it includes a strip holder according to one of the claims 1 to 4, and a frame having a peripheral wall as well as an upper and lower counter surface, the strip holder being inserted into the frame in such a way that the at least one stop is applied to the lower counter surface and the sealing surface presses tightly against an inner surface of the wall.

6. The chamber according to claim 5,
    wherein it also includes a cover for applying to the upper counter surface of the frame and two electrode holders, insertable into this cover.

7. The chamber according to claim 6, wherein the cover includes a bead, which projects into the chamber and limits the inside of the chamber over the gel strips, the outermost lower edge of the bead being applied to one of the sealing lips of the lip seal or an O-ring to form a seal.

8. The chamber according to claim 6,
wherein the electrode holders are implemented so they are insertable into two defined levels and each include an electrode, which is restrictedly movable perpendicular to the surface of a gel strip lying on the carrier surface of the strip holder.

9. The chamber according to claim 8,
wherein the electrodes are implemented as tubes having an open upper opening, a laterally branching electrical contact, and a frit, which partially seals the lower opening.

10. The chamber according to claim 6,
wherein at least one of the electrode holders also includes a sample tube, which is restrictedly movable perpendicular to the surface of a gel strip lying on the carrier surface of the strip holder.

11. 1-D gel electrophoresis method,
wherein a dehydrated gel strip is positioned on the carrier surface of a strip holder, the strip holder including a baseplate which includes the carrier surface—for accommodating a gel strip for separating molecules using gel electrophoresis—which includes at least one stop, offset to a lower level in relation to the carrier surface, and at least one sealing surface, this stop being implemented to be applied to counter surfaces of an electrophoresis chamber, through which offset to a lower level of the stop the installation depth of the strip holder carrying a gel strip into this electrophoresis chamber is determined, and the sealing surface ensuring a sealing installation of the strip holder carrying a gel strip into this electrophoresis chambers
and wherein the at least one stop is imDlemented in one piece with the baseplate and forms at least one stop surface.

12. The method according to claim 11,
wherein a strip holder according to one of claims 3 to 4 is used.

13. The method according to claim 11,
wherein this strip holder is inserted into a frame having a peripheral wall as well as an upper and lower counter surface in such a way that the at least one stop is applied to the lower counter surface and the sealing surface presses tightly against an inner surface of the wall.

14. The method according to claim 13,
wherein the gel strip is layered with rehydration solution in the inside of such a chamber and a sample is applied to the gel strip.

15. The method according to claim 14,
wherein the sample is applied to the gel in a strip when the chamber is open and the chamber is closed with a cover to be applied to the upper surface of the frame and with two electrode holders insertable in this cover, in that the electrode holders are inserted in an upper level, through which one electrode at a time, which are each restrictedly movable perpendicular to the surface of a gel strip lying on the carrier surface of the strip holder, are positioned at an interval to this surface until the sample is diffused into the gel, upon which the electrode holders are lowered to a lower level, due to which the two electrodes come into contact with this surface.

16. The method according to claim 14,
wherein the chamber is closed with a cover to be applied to the upper surface of the frame and with two electrode holders insertable in this cover, in that the electrode holders are inserted into a lower level, through which one electrode at a time and a sample tube, which are each restrictedly movable perpendicular to the surface of a gel strip lying on the carrier surface of the strip holder, come into contact with this surface, after which the sample is drawn into the gel strip from the sample tube while an electrical voltage is applied to the gel.

17. The method according to one of claims 15 or 16,
wherein the gel strips are subjected to electrical high voltage via the electrode until the isoelectric focusing of the molecules in the gel has occurred, the electrical high voltage being generated using a single-channel control device, which regulates the electrical current parameters and, in addition, stores them so they may be called up and displayed on a display screen.

18. A system for automatically performing the method according to claim 11,
wherein it includes a working platform for arranging one or more IEF Chambers.

19. The system according to claim 18,
wherein it includes a robot arm for transferring individual parts of the chambers to and from these IEF chambers as well as a computer for controlling the robot, a single-channel high-voltage control for individual control of the IEF chambers, and a display screen.

* * * * *